United States Patent [19]

Williams

[11] Patent Number: 4,994,910
[45] Date of Patent: Feb. 19, 1991

[54] MODULAR ENDOSCOPIC APPARATUS WITH PROBE

[75] Inventor: P. Michael Williams, San Carlos, Calif.

[73] Assignee: Acuimage Corporation, San Carlos, Calif.

[21] Appl. No.: 376,881

[22] Filed: Jul. 6, 1989

[51] Int. Cl.$^5$ .............................. A61B 1/04; A61B 1/06
[52] U.S. Cl. ............................................ 358/98; 128/6
[58] Field of Search ....................... 358/98; 128/4, 6-9, 128/11

[56] References Cited

U.S. PATENT DOCUMENTS

| | | | |
|---|---|---|---|
| 4,727,416 | 2/1988 | Cooper | 358/98 |
| 4,854,302 | 8/1989 | Allred | 358/98 |
| 4,899,731 | 2/1990 | Takayama | 358/98 |
| 4,905,082 | 2/1990 | Nishigaki | 358/98 |

Primary Examiner—Howard W. Britton
Attorney, Agent, or Firm—Julian Caplan

[57] ABSTRACT

A miniaturized video image device 22 includes a video image sensor 32 provided in optical communication with a probe 40 which is comprised of a rod lens or fiber optics or the like. The probe 40 includes a tip deflection wire 64 for deflecting and positioning the distal end 62 of the probe 40. A balloon 70 is provided adjacent the distal end 62 of the probe 40 in order to assist in positioning the distal end 62 and to allow for the performing of various surgical techniques. Additionally conduits 72, 78 and ports are provided for providing fluids to the distal end 62 in order to flush distal end 62 and for additionally allowing aspiration of fluids from the distal end 62 as a procedure is being performed. In an embodiment the probe 40 is rotatable with respect to the housing 30 containing the image sensor 32 in order to allow the distal end 42 to be deflected in a desired direction.

23 Claims, 3 Drawing Sheets

MODULAR ENDOSCOPIC APPARATUS WITH PROBE

BACKGROUND OF THE INVENTION

The present invention relates generally to an endoscopic apparatus, and more particularly to endoscopes having modular attachments and which are capable of multiple functions.

DESCRIPTION OF THE PRIOR ART

Endoscopy is a well known technique for viewing the internal region of a body not otherwise viewable. Such viewing is accomplished by introducing into the body an endoscope capable of optically communicating visual information regarding the interior of the body to a viewer or video imaging equipment. The endoscope typically is a long, slender body with an image capturing portion at one end (the distal end) and handle or other manipulating devices at the other end (the proximal end). The endoscope typically includes various lenses, a fiber optic cable, a light source, and a camera. The camera is often located in the proximal end since in many cases the camera is larger than the area into which a viewing device may be located (i.e., the camera is larger than the diameter of the endoscope body). The video imaging equipment includes various video processing devices, a video monitor and/or video recorder, which are capable of presenting video information received from the endoscope to a viewer. Thus, a video record of a relatively inaccessible region of the body could be viewed live or from recorded tape.

Advances in the microminiaturization of charge-coupled devices (CCDs), and similar solid state imaging hardware have made possible the reduction in size of the electro-optical endoscope. In addition, the wide variety of available shapes and configurations of endoscope bodies, and the development of flexible endoscopes, allow penetration into more convoluted interior regions of a body. The advent of monolithic CCD arrays and similar image hardware have also improved the image resolution attainable by endoscopic imaging techniques.

Endoscopes have found applications in a wide variety of disciplines, including dentistry, medicine, mechanical repair, aerospace applications, etc.—anywhere there is a need for remote viewing of a small, inaccessible region and/or recording what is seen. Often, activity is required in an area which is not directly viewable. For example, the medical practice of arthroscopic surgery, certain cardio-surgical procedures, etc., are done with remote instruments through the smallest possible opening in the patient. These procedures, which could not be accomplished without a clear view of the work area, are done using the required instruments in conjunction with an endoscope—the operation being done via a video monitor.

In the practice of dentistry, the X-ray machine has been the predominant imaging tool used to record and view dental and periodontal structure. Hand held tools having mirrored surfaces provide visual access by the dentist to many, but not all areas of the mouth not directly viewable. Such tools, of course, have the further limitation that they provide only a small image, and, were such desired, they offer no capability to provide a permanent record of what the dentist sees. U.S. Pat. No. 4,727,416 addresses the dental market with a dental camera which fits into the mouth.

Certain devices are finding their way into the market which allows a doctor to both view regions not directly viewable and to record and monitor any region within the patient. These devices are improving in versatility and accuracy, but still there are significant limitations in the state-of-the-art. For example, the existing art is incapable of providing for varying the field of view and/or angle of view of the device to suit different applications and needs, is incapable of providing adequate illumination of the imaging target area, cannot be adequately sterilized (to prevent cross-contamination), is incapable of rotatably presenting the image to vary the relative up/down orientation; etc.

SUMMARY OF THE INVENTION

Thus, there is a present need in the art for an endoscopic apparatus capable of providing for varying the field of view and/or angle of view of the apparatus to suit different applications and needs, which is capable of rotating in order to present an image for viewing, and which is capable of a high degree of sterilization.

According to a preferred embodiment of the present invention, an endoscope is provided, which is particularly well suited to dental and medical applications, having interchangeable, modular image-gathering elements (or objective elements) to accommodate a variety of applications, a solid-state miniature camera capable of generating video images for real-time viewing and/or recording by a video recorder, a rotatability feature in order to present different images for viewing and further having a probe which is selectably positioned relative to the desired observation site.

Each objective element is generally comprised of a lens or lenses, light source projection optics, and optical interconnection for connecting the objective element to a finger piece. The objective element may be flexible, malleable, or rigid and may be of a variety of sizes and shapes to accommodate varying viewing requirements of the user.

The finger piece is comprised of a body upon which is mounted a video camera arrangement such as a CCD mosaic chip camera, and a connection element capable of receiving an optical connection from the objective element. Provision for immersing the endoscope in a sterilizing solution without affecting the electrical componentry or interconnections is made, for example, by isolating the camera in an optically clear housing, and isolating the interior of the body. A standard ACMI light fitting (or equivalent) may be provided where the light source is to be a fiber-optic connection of a type commonly used in the art.

The output of the chip camera is such that it may be directly input to one of a number of generic video endoscopy systems. Such systems are capable of providing real-time viewing of an image, and optionally may be capable of making a video record of the image on tape or the like.

These features, as well as others, will become more readily apparent from the following detailed description of the preferred embodiment in the accompanying drawings.

DETAILED DESCRIPTION OF THE PREFERRED EMBODIMENT

Figure 1:
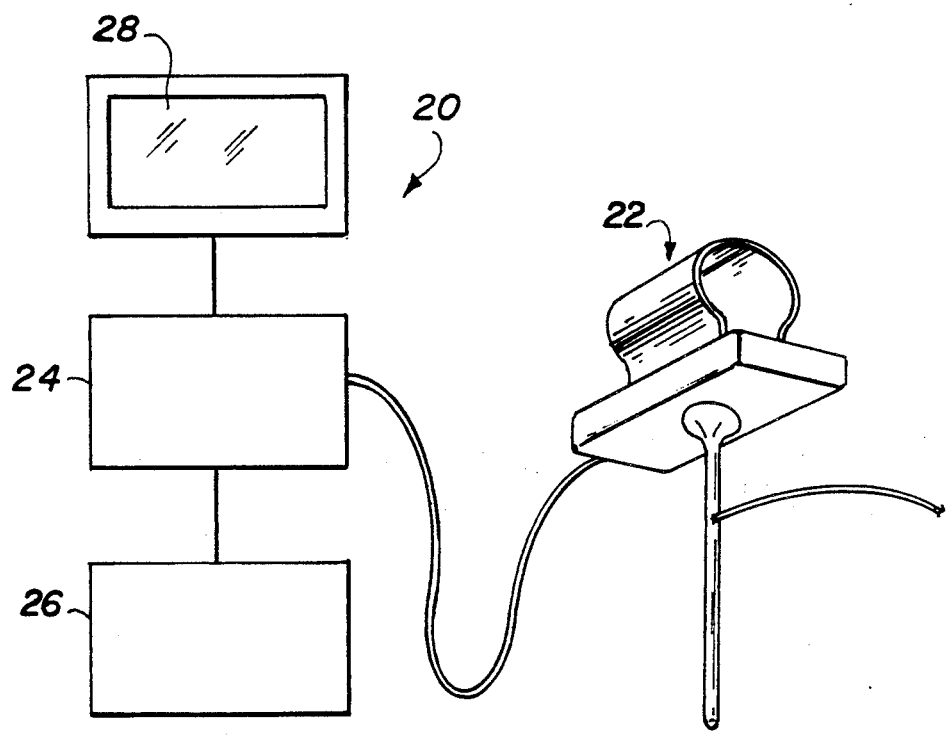
FIG. 1 depicts a schematical representation of the video imaging system of the invention.

With respect to the figures and in particular FIG. 1, a miniaturized video imaging system 20 is depicted. System 20 includes a video imaging device 22 which is provided in communication with a video image processor 24 which is controlled by a video control 26 so that video image can be presented on monitor 28.

Figure 2:
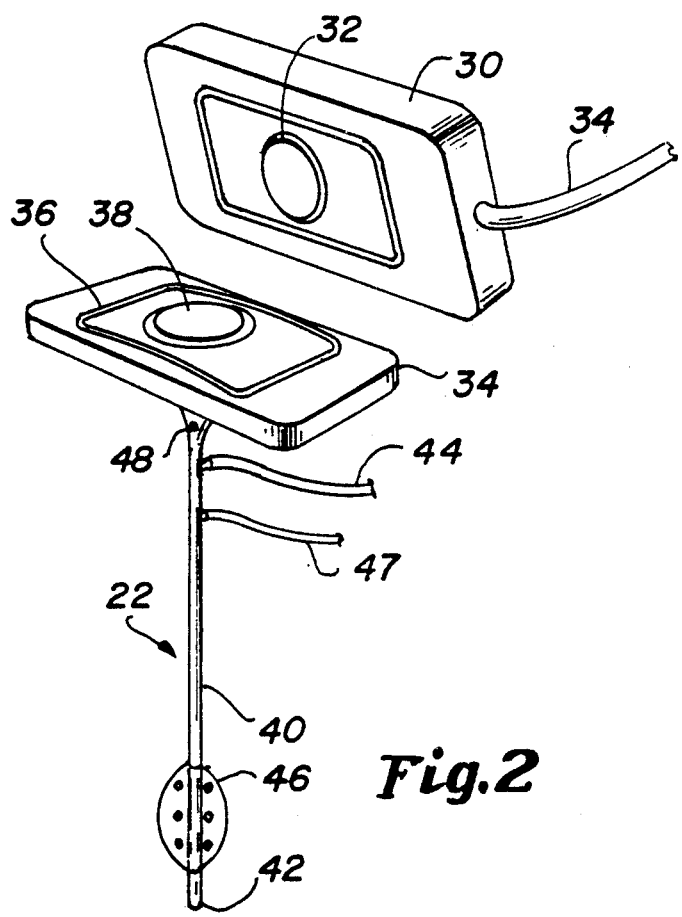
FIG. 2 depicts a perspective view of a video imaging device of the invention.

FIG. 2 depicts a specific embodiment of the video imaging device 22. This video imaging device 22 includes a housing 30 which can, in a preferred embodiment, be comprised of stainless steel. Inside the housing is mounted an imaging sensing device 32 which in a preferred embodiment can be comprised of a charged coupled device (CCD) appropriately sealed in housing 30 so that the external housing can be adequately sterilized. A video image and control cable 34 provides communication to the video processor 24 from the image sensing device 32. A base 34 is rotatably and detachably secured to the housing 30 by appropriate means 36 which can include in a preferred embodiment a magnetic arrangement or a friction arrangement or lens mount arrangement. Mounted on base 34 is a lens system 38 which is positioned adjacent the image sensing device 32 with the base 34 secured to the housing 30. Extending from the base 34 is an elongated optical probe 40 which is in optic communication with the lens system 38. The probe 40 can, in a preferred embodiment, be rigid, flexible or malleable. The probe 34 is comprised of, in a preferred embodiment, rod lenses and/or fiber optic in order to provide a light source to the distal end 42 of the probe and to conduct an image from the distal end 42 of the probe to the lens system 38. The probe 40 is also fitted with a fluid conduit 44 which can be used to provide fluid such as air, water or an appropriate drug to the distal end 42 of the probe 40 and/or selectable to aspirate fluid and substances from the distal end 42 of the probe. A cuff 46 is provided adjacent the distal end 42. This cuff is in communication with a second fluid conduit 47 and can be inflated or deflated through the passage of fluid through conduit 47. An instrumentation port 48 is provided which communicates with a conduit provided in probe 40. Instrumentation port 48 can receive, for example, laser instrumentation for performing various surgical procedures.

Figure 4:
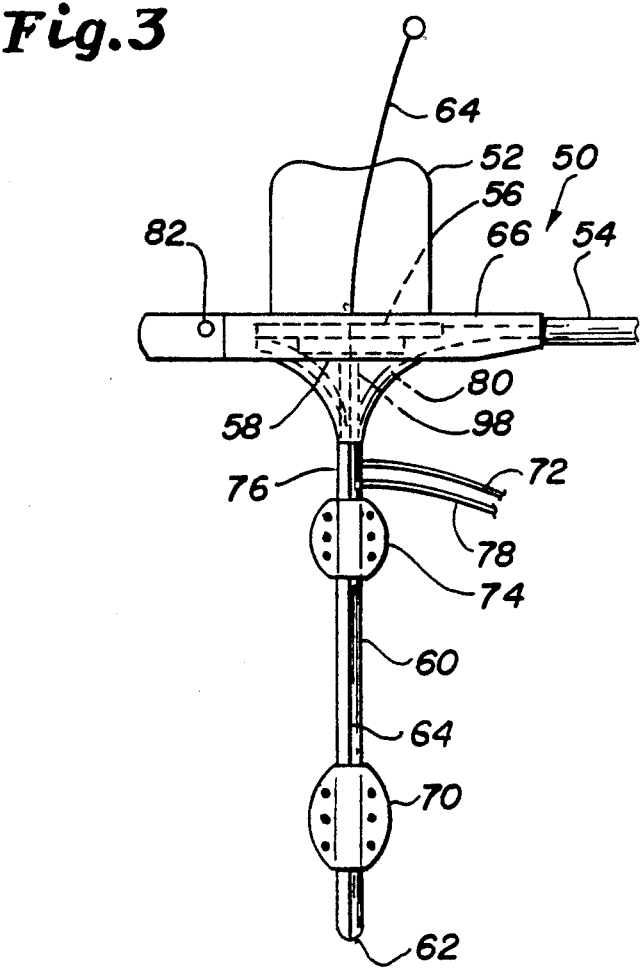
FIG. 4 depicts still another embodiment of the video imaging device of the invention.

FIG. 4 depicts a video imaging device 50. Device 50 includes a finger band 52 which can be disposed about the finger of an operator for selectively positioning the device 50. A video cable 54 is used to communicate with the system 20 and also with a video sensor 56 which can be comprised of a charged couple device or other appropriate sensors. An optical arrangement 58 provides communication between the image sensor 56 and the elongate optical probe 60. Probe 60 can contains an appropriate rod lens and/or fiber optics in order to provide a video image from the distal end 62 of the probe 60 through the optical arrangement 58 to the image sensor 56. A tip deflection wire 64 projects through the base 66 of the device 50 and is provided along the probe 60 and secured to the probe 60 at the distal end 62 in order to be able to displace the distal end by movement of the deflection wire 64. The probe 60 is, as has been stated, flexible. Since the tip of wire 64 is secured to end 62, b y pulling the wire the tip 62 of the probe is pulled toward base 66 and hence deflects.

A balloon 70 is-disposed adjacent the distal end 62 of the probe 60. Balloon 70, in a preferred embodiment, is comprised of a wire mesh arrangement which becomes hot enough to cauterize, for example, human tissue when a electrical current is passed therethrough. The tip deflection wire 64 is electrically conducting and a portion of said wire 64 adjacent the balloon 70 is provided in electrical contact with the balloon 70 in order to provide electrical current thereto. The remaining length of the tip deflection wire 64 is electrically insulated from the rest of the device 50. An appropriate conduit 72 is provided for causing fluid to be communicated to the balloon 70. A second balloon 74 is provided adjacent the proximal end 76 of the probe. A conduit 78 provides appropriate fluid to balloon 74 in order to inflate this balloon in order to reduce or minimize bleeding adjacent the insertion site of the probe.

An appropriate conduit means 80 is provided for allowing a fluid such as air or water to be positioned adjacent the distal end 62 of the probe in order to flush the work site and/or administer drugs at the work site. In addition, fluid and tissues can be aspirated through conduit 80. Instrumentation port 82 is further provided for allowing appropriate surgical instrumentation to be positioned adjacent the distal end 62 of the probe 60.

It is to be understood that a tip deflection wire can be provided to the embodiment 22 in FIG. 2 so that various sites can be viewed by both rotating the probe 40 and deflecting the distal end 42 of the probe 40.

Figure 3:
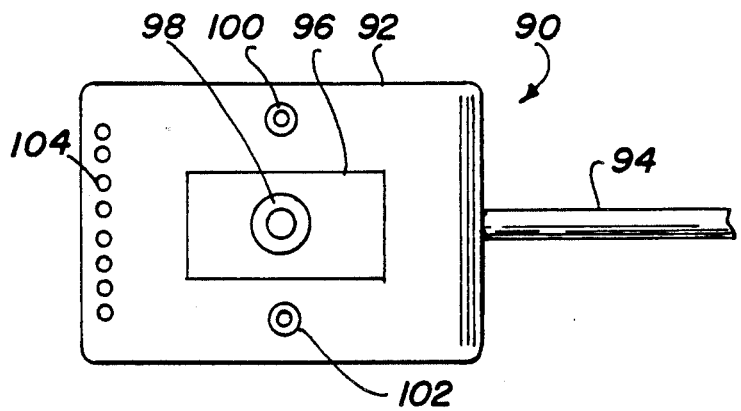
FIG. 3 depicts a side section view of another embodiment of the video imaging device of the invention.

Another embodiment of the video imaging device is shown in FIG. 3 and identified by the number 90. This device 90 includes a body 92 which has projecting therefrom a video cable 94. The video cable communicates with a video imaging device 96 which communicates with a lens arrangement 98. With this embodiment there is no probe extending from the lens arrangement. Adjacent the lens arrangement are two light sources 100 and 102 which are used to illuminate the work site so that an appropriate image can be viewed.

The body is further provided with ports 104 which can function to provide a fluid such as air or water or other fluid across the area to be viewed in order to flush the work site and keep the lens arrangement 98 clear. Additionally, fluids and tissues can be aspirated through these ports.

Figure 7:
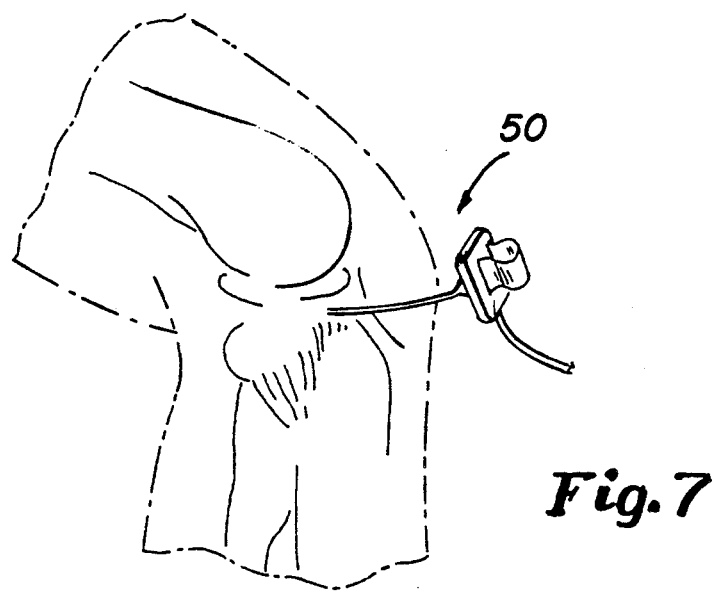
FIG. 7 is a schematic view showing the device of FIG. 2 in use.

FIG. 7 depicts the device 50 as shown in greater detail in FIG. 4, positioned for viewing the knee of a patient.

Figure 8:
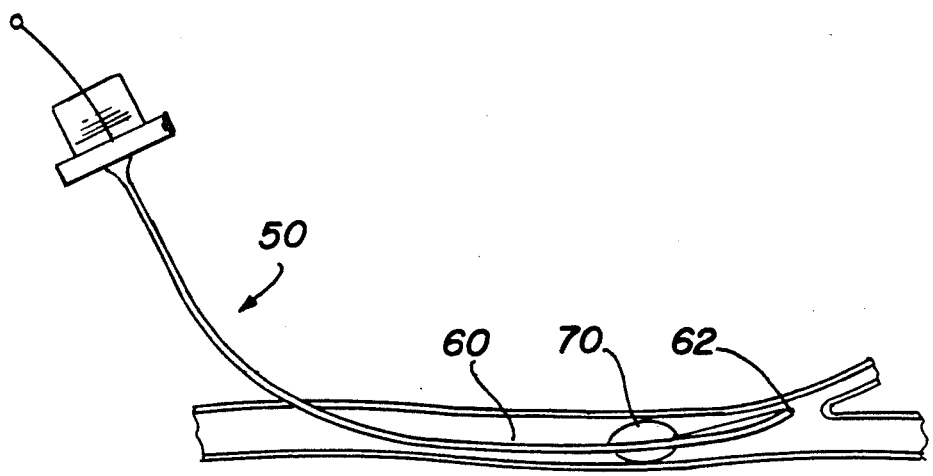
FIG. 8 is a schematic sectional view of the device of FIG. 2 in use.

FIG. 8 depicts an embodiment which is as shown in FIG. 4, provided in a blood vessel in order to seek out and widen a blockage in the vessel. In such an arrangement, the probe 60 is flexible and the deflection wire 64 allows the distal end 62 to be appropriately positioned under observation from a video signal. The balloon 70 can be then dilated to enlarge the blockage and then a current can be passed through the balloon as provided by the deflection wire 64 in order to cauterize the vessel to prevent bleeding and uneven scaring.

FIG. 7 depicts a perspective view of the device which is similar to that of FIG. 3 with the balloon portions removed. FIG. 8 depicts a perspective view of the device of FIG. 4 with a finger band 110 secured thereto.

Figure 5:
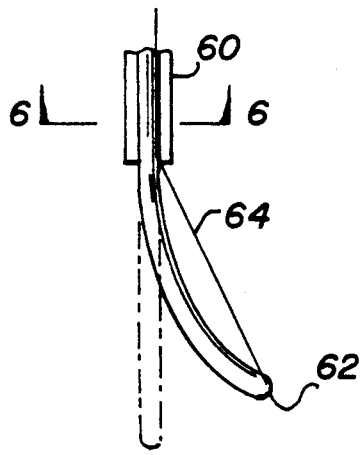
FIG. 5 is an enlarged partial side elevational view of a portion of FIG. 4.
Figure 6:
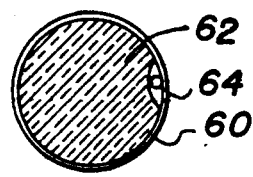
FIG. 6 is a further enlarged sectional view taken substantially along line —6— of FIG. 5.

FIG. 9 depicts a device quite similar to that used in FIG. 5 but applied in a situation where an image of a yet to be born child is being made.

FIG. 10 depicts the distal end of a probe 112 being mounted on a surgical instrument 114.

Industrial Applicability

From the above it can be seen that the operation of the invention allows for the miniaturization of a video imaging device so that such a device can be positioned in otherwise obscure areas in order to view a surgical work site or another work site. It can be seen that the present invention has the distinct advantage of providing an imaging probe which can be positioned through use of a tip deflection wire and which can mount appropriate balloons in order to hold the position of the probe and in order to perform surgical operations such as vessel dillitation, and vessel cauterization or glazing.

It is to be understood that the present invention can be used in other environments such as astronomy systems, with manufacturing and other inspection systems, with recording and information storage devices, with scanning systems, various computer systems and other uses where view imaging is necessary and must be provided in a compact system.

Other objects and advantages of the present invention can be obtained from a view of the figures and the appended claims. It is to be understood that other embodiments of the present invention can be derived which fall within the spirit and scope of the claims.

What is claimed is:

1. A miniaturized video imaging device comprising:
   a body;
   sensing means for sensing an image, which sensing means is mounted in said body;
   probe means for defining an elongate optical probe with a distal end and a proximal end and positionable in otherwise inaccessible areas;
   optical connector means mounted between said probe and said body for optical connecting the proximal end of the optical probe means and the image sensing means; and seal means sealing said sensing means within said body against fluids but exposed to said lens means, said probe means being connected to said body.

2. The video image device of claim 1 wherein said optical connector means includes:
   means for allowing said probe means to be rotated relative to said body.

3. The video image device of claim 1 wherein said probe means is flexible.

4. A device according to claim 1 in which said body and said probe means are unitary.

5. A device according to claim 1 in which said sensing means comprises a charge coupled device.

6. A device according to claim 1 which further comprises digital connecting means on said body whereby said digital connecting means may be manually actuated to maneuver said probe means.

7. A device according to claim 6 in which said digital connecting means comprises a finger band.

8. The video image device of claim 1 including:
   an expandable balloon positioned about said optical probe in close relationship to the distal end of said probe.

9. The video image device of claim 8 wherein:
   said balloon is comprised of a material so that the balloon is flexible and collapsible.

10. The video imaging device of claim 8 includes:
    a second expandable balloon positioned about said optical probe in close relationship to said proximal end of said probe.

11. A miniaturized video imaging device according to claim 1 further comprising:
    means for providing a fluid carrying conduit along said probe means and said fluid conduit means defining a port located adjacent the distal end of said probe means.

12. The video image device of claim 11 which further comprises
    second conduit means disposed along said probe means and defining a port adjacent said distal end for directing instrumentation at a site adjacent said distal end.

13. The video device of claim 11 wherein said optical connector means includes:
    means for allowing said probe means to be rotated in relation to said body and magnetic means attaching said probe means to said body.

14. A device according to claim 1 in which said probe means comprises fiber optics and rod lenses to conduct light to the distal end of said probe and conduct an image from said distal end and said lens means, respectively.

15. A device according to claim 14 which further comprises a fluid conduit in said probe means extending through said probe means to said distal end.

16. A device according to claim 14 which further comprise an instrumentation port and an instrumentation conduit in said probe means, sad conduit extending to the distal end of said probe means.

17. A device according to claim 1 in which said probe means is flexible and which further comprises deflection means for selectively deflecting said distal end of said probe means.

18. The video image device of claim 17 wherein said deflection means includes:
    an elongate deflection wire with a distal end and a proximal end, said distal end secured to the distal end of said optical probe means and disposed along said optical probe means and said proximal end disposed adjacent said body.

19. A device according to claim 17 in which said optical connector means comprises means whereby said probe means ay be rotated relative to said body.

20. A device according to claim 1 in which said probe means has a base on its proximal end and which further comprises connector means for detachably connecting said base to said body.

21. A device according to claim 20 in which said connector means comprises a groove in said body and a ridge on said base frictionally fitting in said groove.

22. A device according to claim 20 in which said connector means is magnetic.

23. A device according to claim 20 in which said optical connector means comprises a lens mounted on said base.

* * * * *